United States Patent
De Schrijver

(10) Patent No.: US 6,414,177 B2
(45) Date of Patent: Jul. 2, 2002

(54) METHOD OF PRODUCING CYCLOPENTANONE NITRILES

(75) Inventor: Johny Edmond De Schrijver, Sint-Niklaas (BE)

(73) Assignee: Degussa-Huls AG, Frankfurt am MAin (DE)

( * ) Notice: Subject to any disclaimer, the term of this patent is extended or adjusted under 35 U.S.C. 154(b) by 0 days.

(21) Appl. No.: 09/811,485

(22) Filed: Mar. 20, 2001

(30) Foreign Application Priority Data

Mar. 25, 2000 (DE) .......................... 100 15 063

(51) Int. Cl.⁷ ............................................. C07C 253/00
(52) U.S. Cl. ...................................................... 558/336
(58) Field of Search .......................................... 558/336

(56) References Cited

U.S. PATENT DOCUMENTS

| | | |
|---|---|---|
| 4,016,109 A | 4/1977 | Cohen et al. |
| 5,091,554 A | 2/1992 | Huthmacher et al. |

*Primary Examiner*—Taofig Solola
*Assistant Examiner*—Joseph Murray
(74) *Attorney, Agent, or Firm*—Pillsbury Winthrop LLP

(57) ABSTRACT

A method for producing compounds of the general formula (I)

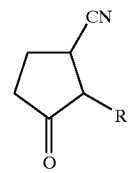

(I)

in which R is a linear or any branched ($C_1$–$C_{18}$) alkyl group, from compounds of the general formula (II)

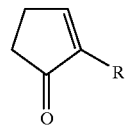

(II)

that are reacted in the presence of hydrogen cyanide or a precursor producing hydrogen cyanide in situ and of catalytic amounts of base. The presence of another polar solvent is not necessary. Compounds of formula (I) are important intermediates for perfumes and aromatic substances.

9 Claims, No Drawings

METHOD OF PRODUCING CYCLOPENTANONE NITRILES

FIELD OF THE INVENTION

The present invention relates to a method of producing compounds of the general formula (I).

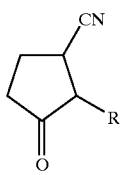

(I)

These nitriles are valuable intermediates for the production of perfumes and aromatic substances.

BACKGROUND OF THE INVENTION

According to U.S. Pat. No. 4,016,109, such compounds are obtained either under acidic conditions by the Michael addition of cyanide ions or by the base-catalyzed addition of hydrogen cyanide released from acetone cyanohydrin in situ to the corresponding cyclopentenone. That method has the disadvantage that the hydrogen cyanide must first be converted into the cyanohydrin and must subsequently be released again from the latter. Moreover, an organic solvent is present in this reaction. It is advantageous in large-scale methods for the methods to be carried out economically, which means, among other things, that as little feed material as possible is used in the methods.

SUMMARY OF THE INVENTION

The present method therefore has the object of providing another method of producing the compounds of general formula (I) that in particular permits the production of the compounds of formula (I) in a more economical manner.

In order to produce compounds of the general formula (I)

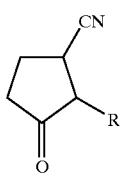

(I)

in which R is a linear or any branched ($C_1$–$C_{18}$) alkyl group, a start is made from compounds of the general formula (II)

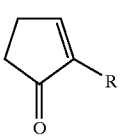

(II)

in which R has the significance indicated above, reacts the compounds in the presence of hydrogen cyanide or a precursor producing hydrogen cyanide in situ and in the presence of catalytic amounts of base, it is totally surprisingly possible to carry out the reaction in the absence of any added organic solvent.

This is surprising since the bases used are also salt-like compounds that are normally only soluble in very polar, organic solvents such as, e.g., methanol, and there was the danger of these substances being withdrawn from the reaction by precipitation and not being able to develop any action any longer. Thus, by way of example, in DE 39 42 371 (corresponding to U.S. Pat. No. 5,091,554) and DE 1 00 85 871, the presence of polar, organic solvents (DMF or an excess of isophorone) is preferred in a comparable reaction. Under the given circumstances it is therefore surprising that under these conditions no significant side reactions such as, e.g., aldol or Michael addition of enone (II) and nitrile (I) or polymerization of hydrogen cyanide take place. Totally surprisingly, a yield of >94% nitrile (I), that is better than that obtained with the state of the art, is achieved with the reaction conditions in accordance with the invention.

In principle, all organic and inorganic bases familiar to an expert in the art for this purpose can be considered as bases to be used, in as far as they display a sufficient effect for the catalysis of the Michael addition. This can be readily explained in routine experiments. Note, by way of example, the experiments cited in DE 39 42 371. It is preferable to use advantageous, inorganic substances such as, e.g., NaOH, $Na_2CO_3$, $Ca(OH)_2$, etc. as bases. LiOH is preferably used.

The amount of base to be used is a function of its effectiveness in the reaction medium and the possibility of minimizing the expense of feed substances. The base is preferably used in an amount of 0.01 to 10 molar %, preferably 0.1 to 5 molar %, especially preferably 0.5 to 5 molar % relative to the enone (II).

The temperature can be selected as desired in the reaction under consideration. It should be regulated in such a manner that the reaction takes place as rapidly as possible but that, on the other hand, as few byproducts as possible are formed. The reaction is advantageously carried out at a temperature of 10°–120° C., preferably 30°–80° C.

The present invention is concerned in a further embodiment with the use of the nitrile (I) produced in accordance with the invention in a method of producing perfumes with the general formula (III)

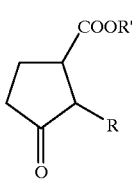

(III)

in which R has the significance indicated above and R'=H, Na, K, Li, $Ca_{1/2}$, $Mg_{1/2}$, or a linear or branched ($C_1$–$C_{18}$)-alkyl group. The nitrile (I) is preferably not isolated in an intermediate manner but rather the conversion of the nitrile function immediately follows its production. This only becomes possible as a result of the fact that the nitrile (I) can be produced in extremely pure form based on the method of the invention and that any other byproducts created do not contaminate the perfume that is finally obtained. The further processing of (I) to (III) can take place analogously with U.S. Pat. No. 4,016,109.

In the framework of the invention a ($C_1$–$C_{18}$) alkyl group that is linear or branched in any way denotes an alkyl group with 1 to 18 C atoms that comprises all theoretically possible bonding isomers such as, e.g., methyl, ethyl, propyl, isopropyl, n-butyl, sec-butyl, isobutyl, tert.-butyl, pentyl, hexyl, heptyl, octyl, nonyl, decyl, undecyl, dodecyl, etc.

DETAILED DESCRIPTION OF THE PREFERRED EMBODIMENTS

Example:

Laboratory procedure for the production of 2-n-hexyl-3-cyanocyclopentanone

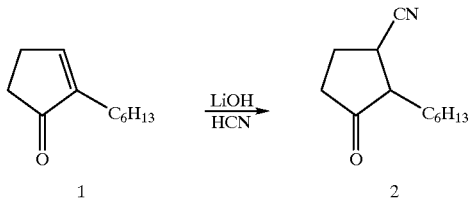

Lithium hydroxide (4.07 g; 0.17 mole) is dosed at 40° C. to 2-n-hexylcyclopentenone (1402.8 g; 8.435 mole). Hydrogen cyanide (251.6 g; 9.28 moles, 1.1 eq.) is dosed in at 40° C. in 30 minutes, during which the temperature rises to 62° C. The mixture is additionally heated 2 hours longer at 55° C. The yield of 2-n-hexyl-3-cyanocyclopentanone is 94.3% (1534.3 g).

What is claimed is:

1. A method for producing a compound of general formula (I)

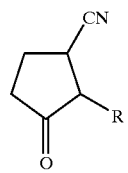

(I)

in which R is a linear or branched ($C_1$–$C_{18}$) alkyl group, from a compound of general formula (II)

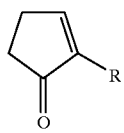

(II)

in which R has the significance indicated above, in the presence of hydrogen cyanide or a precursor producing the hydrogen cyanide in situ and in the presence of catalytic amounts of base, comprising:

carrying out the method in the absence of any added organic solvent.

2. The method according to claim 1, comprising using LiOH as the base.

3. The method according to claim 1, wherein the base is used in an amount of 0.01 to 10 molar %, relative to the compound of formula (II).

4. The method according to claim 3, wherein the base is used in an amount of 0.1 to 5 molar % relative to the compound of formula (II).

5. The method according to claim 3, wherein the base is used in an amount of 0.5 to 5 molar % relative to the compound of formula (II).

6. The method according to claim 1, comprising carrying out the method at a temperature of 10°–120° C.

7. The method according to claim 6, comprising carrying out the method at a temperature of 20°–100° C.

8. The method according to claim 6, comprising carrying out the method at a temperature of 30°–80° C.

9. A method for producing a compound of formula (I)

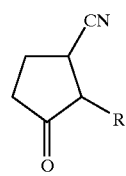

(I)

in which R is a linear or branched ($C_1$–$C_{18}$) alkyl group, comprising reacting a compound of formula (II)

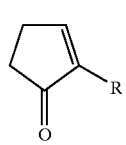

(II)

In which R has the significance indicated above, with hydrogen cyanide in the presence of catalytic amounts of base, and in the absence of any added organic solvent.

* * * * *